(12) United States Patent
Gilchrist et al.

(10) Patent No.: US 6,404,907 B1
(45) Date of Patent: Jun. 11, 2002

(54) METHOD FOR SEQUENCING NUCLEIC ACIDS WITH REDUCED ERRORS

(75) Inventors: Rodney D. Gilchrist, Oakville; James M. Dunn, Scarborough, both of (CA)

(73) Assignee: Visible Genetics Inc., Toronto (CA)

( * ) Notice: Subject to any disclaimer, the term of this patent is extended or adjusted under 35 U.S.C. 154(b) by 0 days.

(21) Appl. No.: 09/345,613

(22) Filed: Jun. 25, 1999

Related U.S. Application Data (60) Provisional application No. 60/090,887, filed on Jun. 26, 1998.

(51) Int. Cl.$^7$ .................................................. G06K 9/00
(52) U.S. Cl. ........................ 382/129; 382/173; 382/190; 435/6
(58) Field of Search ................................ 435/6; 436/86, 436/89; 364/500; 392/129, 173, 190

(56) References Cited

U.S. PATENT DOCUMENTS

| | | | |
|---|---|---|---|
| 4,811,218 A | | 3/1989 | Hunkapiller et al. |
| 4,865,968 A | | 9/1989 | Orgel et al. |
| 5,124,247 A | | 6/1992 | Ansorge |
| 5,273,632 A | | 12/1993 | Stockham et al. |
| 5,308,751 A | | 5/1994 | Ohkawa et al. |
| 5,710,628 A | | 1/1998 | Waterhouse et al. |
| 5,712,476 A | | 1/1998 | Renfrew et al. |
| 5,733,729 A | * | 3/1998 | Lipshutz .......................... 435/6 |
| 5,776,737 A | | 7/1998 | Dunn |
| 5,786,142 A | | 7/1998 | Renfrew et al. |
| 5,849,542 A | * | 12/1998 | Reeve et al. ................ 435/91.1 |
| 5,853,979 A | | 12/1998 | Green et al. |
| 5,916,747 A | | 6/1999 | Gilchrist et al. |
| 6,083,699 A | * | 7/2000 | Leushner et al. ............... 435/6 |
| 6,195,449 B1 | * | 2/2001 | Bogden et al. .............. 382/129 |

FOREIGN PATENT DOCUMENTS

| | | |
|---|---|---|
| EP | 86104822.1 | 10/1986 |
| EP | 91118244.2 | 3/1992 |
| EP | 93250264.4 | 4/1994 |
| GB | 8925772.9 | 11/1989 |
| WO | WO 9741259 | 11/1997 |
| WO | WO 9800708 | 1/1998 |
| WO | WO 9811258 | 3/1998 |

OTHER PUBLICATIONS

Dear and Staden, A sequence assembly and editing program for efficient management of large projects, Nucleic Acids Research, vol. 19, No. 14, 3907–3911, Oxford University Press, 1991.

Plaschke, Voss, Hahn, Ansorge, and Schackert, Doublex Sequencing in Molecular Diagnosis of Hereditary Diseases, BioTechniques 24:838–841, May 1998.

John M. Bowling, et al., "Neighboring Nucleotide Interationcs During DNA Sequencing Gel Electrophoresis", 1991 Oxford University Press, Nucleic Acids Research, vol. 19, No. 11.

R.L. Miller and T. Ohkawa, "Chain Terminator Sequencing of Double–Stranded DNA With Build–in Error Correction", Genereal Atomics Project 4422, Jul. 1991.

C. Tibbits, et al., "Neural Networks For Automated Base-calling of Gel–based DNA sequencing Ladders".

Allan M. Maxam and Walter Gilbert, "A New Method For Sequencing DNA", Proc. Natl. Acad. Sci. USA, vol. 74, No. 2, pp. 560–564, Feb. 1977, Biochemistry.

Stefan Wiemann, "Simultaneous On–Line DNA Sequencing on Both Strands with Two Fluorescent Dyes", Analytical Biochemistry 224, 117–121(1995).

Ulf Landegren, et al., "DNA Diagnostics—Molecular Techniques and Automation", Science, vol. 242, Oct. 14, 1988.

Lance B. Koutney and Edward S. Yeung, "Automated Image Analysis for Distortion Compensation in Sequencing Gel Electrophoresis", 1369 Applied Spectroscopy, 46(1992) Jan., No. 1, Frederick, M.D. US, vol. 46, No. 1, 1992.

James B. Golden, III, et al., "Pattern Recognition for Automated DNA Sequencing: I. On–line Signal Conditioning and Feature Extraction for Basecalling".

Michael C. Giddings, et al., "An Adaptive, Objective Oriented Strategy For Base Calling In DNA Sequence Analysis", 4530–4540, Nucleic Acids Research, 1993, vol. 21, No. 19. 1993 Oxford University Press.

\* cited by examiner

*Primary Examiner*—Marianne P. Allen
(74) *Attorney, Agent, or Firm*—Oppedahl & Larson LLP

(57) ABSTRACT

Nucleic acid polymers are sequenced by obtaining forward and reverse data sets for forward and reverse strands of a sample nucleic acid polymer. The apparent base sequences of these forward and reverse sets are determined and the apparent sequences are compared to identify any deviations from perfect complementarity. Any such deviation presents a choice between two bases, only one of which is correct. A confidence algorithm is applied to the peaks in the data sets associated with a deviation to arrive at a numerical confidence value for each of the two base choices. These confidence values are compared to each other and to a predetermined threshold, and the base represented by the peak with the better confidence value is assigned as the "correct" base, provided that its confidence value is better than the threshold. The confidence value takes into account at least one, and preferably more than one of several specific characteristics of the peaks in the data set that were not complementary.

9 Claims, 6 Drawing Sheets

| RESULT | TEXT 1 | TEXT 2 | REFERENCE TEXT | CONFIDENCE VALUE * | |
|---|---|---|---|---|---|
| | | | | SIGNAL 1 | SIGNAL 2 |
| a | a | a | b | 80% | 60% |
| a | a | b | a | 80% | 60% |
| a | a | b | c | 80% | — |
| a | a | — | b | 40% | — |
| b/a | a | — | b | | |

\* CONFIDENCE THRESHOLD = 50%

METHOD FOR SEQUENCING NUCLEIC ACIDS WITH REDUCED ERRORS

This application claims priority from U.S. Provisional Appl. No. 60/090,887, filed Jun. 26, 1998, which is incorporated herein by reference.

BACKGROUND OF THE INVENTION

During routine sequencing of DNA from samples (such as HIV genotyping after RT-PCR conversion from RNA to DNA), normally only one strand (forward or reverse) of the DNA is actually sequenced. In this case, the researcher must decide whether the output signal, and the resulting basecall is accurate based on their experience and skill in reading sequence signals. If the signal and resulting basecall is of questionable reliability, then the researcher must start the sequencing run again in the hope of obtaining a better signal.

In some cases, the forward and reverse stands are both sequenced, such as by using two dyes on a MICROGENE CLIPPER sequencer manufactured by Visible Genetics Inc. Forward and reverse strand sequencing provides the researcher with more information and allows the researcher to evaluate the quality and reliability of the data from both strands. If the bases on both strands complement each other as expected, then this helps to confirm the reliability of the sequence information. However, in some instances, after the signal data from sequencing is assigned a base (e.g. A, C, G or T), the corresponding base on the opposite strand does not match. If the signal and resulting basecall is of questionable reliability, then the researcher must start the sequencing run again in the hope of obtaining better signal. Alternatively, the researcher might manually review ("eyeball" analysis) the signal data from both the forward and reverse strands and make a decision on which strand's data was more reliable. Unfortunately, any such decision will vary between individual researchers and can lead to inconsistent determination of reliablity within the same sequencing run. Furthermore, this kind of eyeball analysis requires special training which makes it poorly suited for application in routine diagnostic applications.

It would therefore be desirable to have a method for sequencing nucleic acid polymers in which discrepancies can be resolved using automated procedures, i.e. using computerized data analysis. It is an object of the present invention to provide such a method, and an apparatus for performing the method.

SUMMARY OF THE INVENTION

In accordance with the invention, nucleic acid polymers are sequenced in a method comprising the steps of
  (a) obtaining forward and reverse data sets for forward and reverse strands of the sample nucleic acid;
  (b) determining the apparent sequence of bases for the forward and reverse data sets;
  (c) comparing the apparent forward and reverse sequences of bases for perfect complementarity to identify any deviations from complementarity in the apparent sequence, any such deviation presenting a choice between two bases, only one of which is correct;
  (d) applying a confidence algorithm to peaks in the data set associated with a deviation to arrive at a numerical confidence value; and
  (e) comparing each numerical confidence value to a predetermined threshold and selecting as the correct base the base represented by the peak which has the better numerical confidence value, provided that the numerical confidence value is better than the threshold.

The confidence algorithm takes into account at least one, and preferably more than one of several specific characteristics of the peaks in the data sets that were not complimentary.

BRIEF DESCRIPTION OF THE DRAWING

The invention will be described with respect to a drawing in several figures, of which.

DETAILED DESCRIPTION OF THE INVENTION

The purpose of the present invention is to provide a novel method and system for the reduction of errors in sequencing data, and in particular to provide a method and system which can automate the process of reconciling forward and reverse strand sequences to readily provide sequencing results of improved quality.

Figure 1:
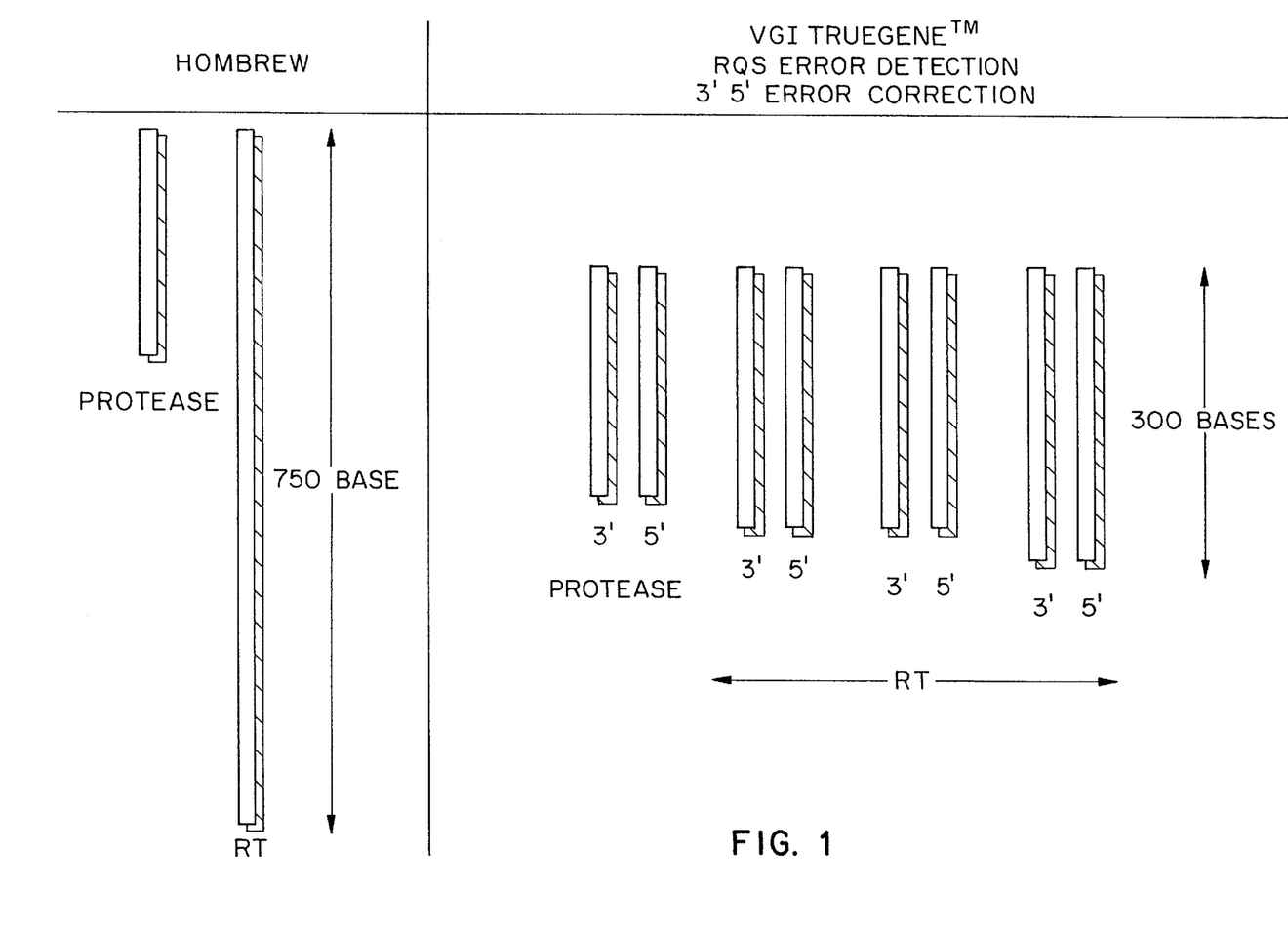
FIG. 1 shows four regions of the HIV-1 genome sequenced in the analysis of HIV according to the invention.

In the present disclosure, the invention is illustrated using sequence data taken from the TruGene HIV-1 Assay manufactured by Visible Genetics Inc. In this case, data traces containing sequence information for one amplicon from the Protease region and three amplicons from the reverse transcriptase (RT) region as shown in FIG. 1 were considered. The reference to this sequence is provided for purposes of example only, however, and to demonstrate the efficacy of the invention. Thus, in a broader sense, the present invention may be applied to the sequencing and error correction of sequencing data for any polynucleotide, including DNA and RNA sequences for any gene or gene fragment.

Figure 2:
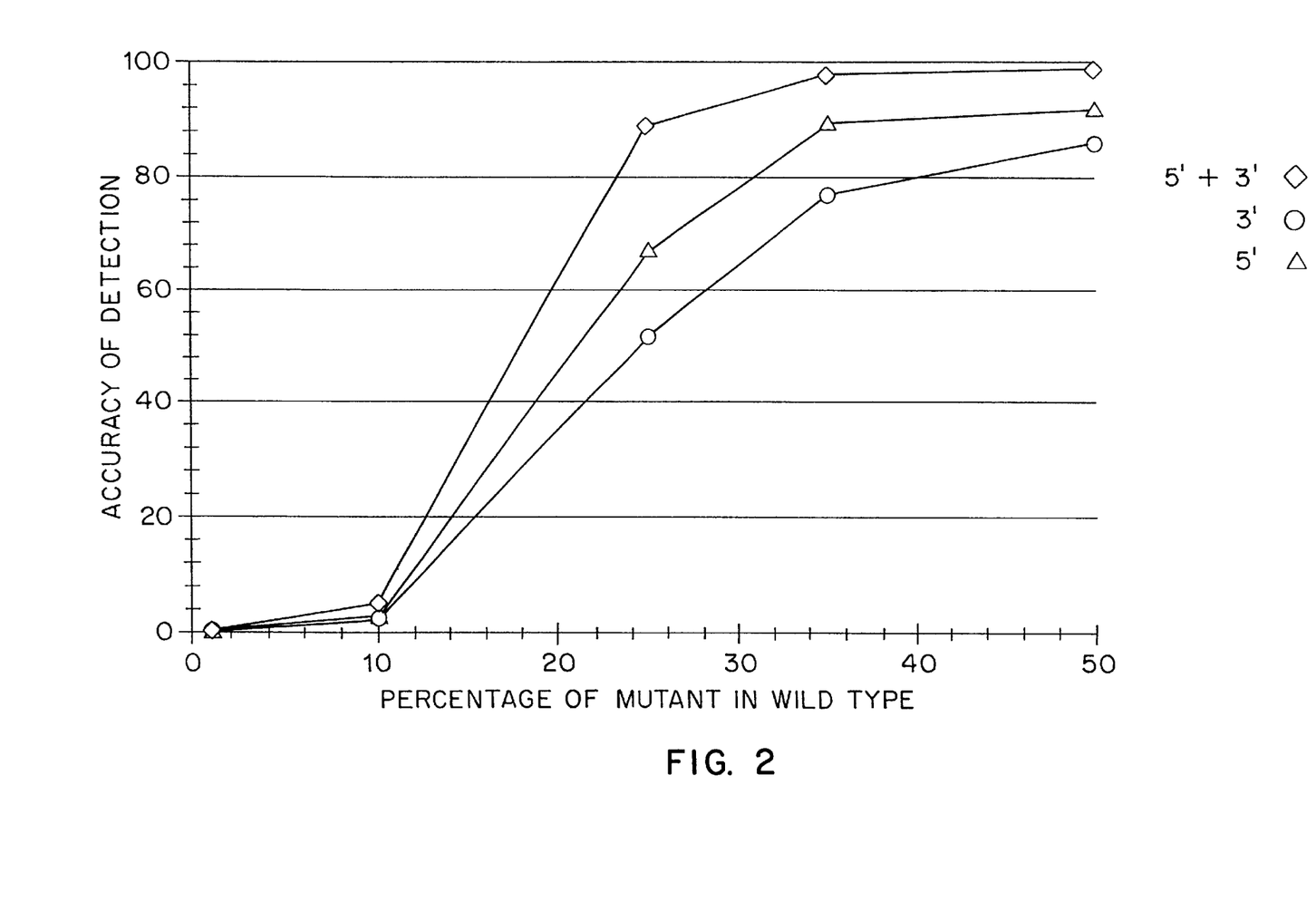
FIG. 2 shows the improvement in accuracy in selecting one of two HIV species using both forward and reverse strands.

Error rates in HIV mutation sequencing are in the range of 5 errors/1000 bases sequenced or higher for many homebrew sequencing methods (single strand). Using the method of the invention these rates are substantially reduced to provide error rates that routinely are as low as 5 errors/100,000 bases and may reach levels as low as 2.5/1000000 bases for a 300 base call. FIG. 2 shows the improvement in accuracy in detecting one of two HIV species using both forward and reverse strands.

The method of determining the sequence of a sample polynucleotide in accordance with the invention involves the following basic steps:
  (a) obtaining forward and reverse data sets for the sample polynucleotide;
  (b) identifying the sequence of bases within the forward and reverse data sets;

(c) comparing the sequence of bases within the forward and reverse data sets to identify any deviations from perfect complementarity in the sequences as determined for the two sets; and (d) applying a confidence algorithm to each deviation to select the correct base from between the choices presented by the identified forward and reverse sequence.

A variety of procedures for obtaining the forward and reverse data sets for the sample polynucleotide are known, and all can be applied in the present invention. In general, the sample polynucleotide or a complementary copy of the sample polynucleotide is combined with a sequencing primer which is extended using a template-dependent polymerase enzyme in the presence of a chain-terminating nucleotide triphosphate (e.g. a dideoxynucleotide) to produce a set of sequencing fragments the lengths of which reflect the positions of the base corresponding to the dideoxynucleotide triphosphate in the extended primer. By preparing one set of fragments for each type of base (e.g. A, C, G and T), the complete sequence for the sample polynucleotide is determined. Forward and reverse sequences are obtained by utilizing two primers which hybridize to the two strands of a duplex DNA molecule.

The preparation of fragment mixtures providing forward and reverse sequencing data sets can be performed as individual reactions, or it can be concurrent. In a concurrent procedure, forward and reverse primers with different labels are extended in the same reaction mixture. This process can involve a single extension cycle as disclosed by Wiemann et al., *Anal. Biochem* 224: 117–121 (1995), or multiple bi-directional cycles (preferably using CLIP™sequencing chemistry, Visible Genetics Inc. ) as described in International Patent Publication No. WO 97-41259 entitled "Method for sequencing of nucleic acid polymers" each of which are incorporated herein by reference. The process can also involve multiple bi-directional cycles as described in U.S. patent application Ser. No. 09/009,483,now issued as U.S. Pat. No. 6,083,699, incorporated herein by reference to the extent permitted. Thus, fragment mixtures reflecting the sequence of the forward and reverse strands of the same polynucleotide are obtained by multiple cycles of a primer extension reaction in which two differently and distinguishably labeled primers are extended in the presence of chain terminator nucleotides in a single reaction mixture. Preferred fragment mixtures utilize fluorescent labels which are detected following electrophoretic separation to produce a forward and reverse data trace for each base position.

The next step in the method of the invention is the identification of the apparent base sequence for both the forward and reverse strands of the sample polynucleotide, a process sometimes referred to as "base-calling." The process of base-calling is theoretically quite straightforward, requiring nothing more than the sequential reading of the bases from the overlapping data traces to produce a list of bases reflecting the sequence. In practice, the process is more complicated, because of departures of actual data from the theoretical ideal. As for the initial generation of the data traces, there are various methods known for dealing with these complications to facilitate automated base-calling from real data, including those disclosed in U.S. Pat. Nos. 5,365,455 and 5,502,773, which are incorporated herein by reference.

A preferred base-calling technique is that disclosed in U.S. Pat. No. 5,853,979 entitled "Method and system for DNA sequence determination and mutation detection with reference to a standard" and International Patent Publication WO 97-02488 entitled "Method and system for DNA sequence determination and mutation detection," each of which are incorporated herein by reference. In this method, a fragment pattern representing the positions of a selected nucleic acid base within the polymer as a function of migration time or distance is evaluated to determine one or more "normalization coefficients." These normalization coefficients reflect the displacement, stretching or shrinking, and rate of stretching or shrinking of the fragment pattern, or segments thereof, which are necessary to obtain a suitably high degree of correlation between the fragment pattern and a standard fragment pattern which represents the positions of the selected nucleic acid base within a standard polymer actually having the known sequence as a function of migration time or distance. The normalization coefficients are then applied to the fragment pattern to produce a normalized fragment pattern which is used for base-calling in a conventional manner.

The process of comparing the experimental fragment pattern and the standard fragment pattern to arrive at normalization coefficients can be carried out in any number of ways without departing from the present invention. In general, suitable processes involve consideration of a number of trial normalizations and selection of the trial normalization which achieves the best fit in the model being employed. It will be understood, however, that the theoretical goal of achieving an exact overlap between an experimental fragment pattern and a standard fragment pattern may not be realistically achievable in practice, nor are repetitive and time consuming calculations to obtain perfect normalization necessary to the successful use of the invention. Thus, when employing this method to facilitate base-calling, the term "high degree of normalization" refers to the maximization of the normalization which is achievable within practical constraints. As a general rule, a point-for-point correlation coefficient calculated for normalized fragment patterns and the corresponding standard fragment pattern of at least 0.8 is desirable, while a correlation coefficient of at least 0.95 is preferred.

The result of the base-calling is two lists of bases, one for the forward strand and one for the reverse strand. Each list contains an indication of the base at a particular location (e.g. one-letter indications A. C, G and T). In some instances, a list may include one or more blanks. Such blanks are inserted by the alignment program to maximize the extent of alignment and take into account the fact that insertions or deletions within one strand may result in a shift of one portion of the strand relative to the corresponding portion of the other strand. These two lists are suitably stored in a data processor performing the sequence analysis as text files. The next step is the comparison of these two text files to determine whether there are any deviations from the theoretically expected perfect complementarity. This comparison process can be performed by any of several methods. Common to these methods is the appropriate alignment of the text listings of bases to a common starting point. This alignment involves an iterative testing of various alignment options to arrive at the best alignment. Iterative routines for accomplishing this alignment have been disclosed by Needleman et al., "A general method applicable to the search for similarities in amino acid sequences of two proteins" *J. Mol. Biol.* 48: 443–453 (1970) and Smith et al., "The identification of common molecular subsequences" *J. Mol. Biol.* 147: 195–197 (1981).

In a first approach, the text file listings of the forward strand and the reverse strand are each aligned with a text file listing of a standard sequence for the sample polynucleotide being sequenced (eg. HIV-1 wild-type sub-type B in the case of the HIV example discussed below). Alternatively, the text file listings for the forward and reverse strands can be aligned to each other. It will be appreciated that the use of text files is only one option, however, and that the alignment may occur between the experimental data sets, or between the experimental data sets and a reference data set.

The important aspect is that the alignment step produce information which will allow a determination of whether or not there is a deviation in the sequence of the forward and reverse strands from the expected complementarity. When such a deviation is detected, the method of the invention provides an automated system for selecting between the options presented and generating a "correct" sequence. This selection process can take place in several steps using a confidence algorithm.

The confidence algorithm is used to assign a confidence value to each base in the forward or reverse text listing that is not confirmed by the other listing. The confidence value is a measure of the likelihood that a particular base identified in a text listing is the correct base. The confidence algorithm determines the confidence value for a peak by taking into account a variety of factors which reflect the quality of the data traces. Specific factors include:

1. separation distance between peaks;
2. regularity/evenness of peak separation;
3. peak height compared to neighbors (higher confidence if similar);
4. peak area compared to neighbors (higher confidence if similar);
5. distance to neighbors compared to the local average distance to neighbors;
6. resolution of the peak (lower confidence for lower resolution); and
7. signal-to-noise ratio in the region around the peak (lower confidence as the peak's size is more similar to the noise level).

The number of characteristics and the particular characteristics considered are a matter of design choice which is driven by the performance of the combination of chemistry and instrumentation which is used. In some systems, it may be the case that a few characteristics (e.g. two) are particularly sensitive to the causes of error, in which case determination of a numerical confidence value based on these characteristics is sufficient.

In a preferred embodiment, all of these factors are included in a weighted combination to arrive at the confidence value, although the use of less than all of the factors may be considered, particularly where two factors are similar (such as peak height and peak area). The confidence value is also lowered in some recognized special cases:

peak is a heterozygote;
more than two overlapping peaks; or
the peak is small compared to its neighbors.

The system evaluating the data traces may also attempt to fit groups of peaks to the signal when the peaks are low resolution. These fitted peaks are also assigned confidence values using the above.

The specific weighting applied to each factor will vary to some extent with the configuration of the sequencing instrument employed and the chemistry used since each experimental combination will tend to produce different variability which affects the accuracy of the base call. Thus, for example, some sequencing chemistries are prone to greater variability in peak height than others, such that variations in peak height might be of less significance in the confidence algorithm. Initial determination of the appropriate weighting for a given system can be done using multiple calibration runs with a known sequence and varying the weight given to the different factors to arrive at the most consistent and error-free results. In a preferred embodiment, the weights given to the different factors are updated heuristically as experimental sequences are determined.

Once the weights to be given to the confidence factors are determined, an overall numerical confidence value is calculated for each peak which indicates deviations from the expected match between the forward and reverse sequences. This calculated confidence value is then compared to a predetermined threshold value to determine whether the confidence value is sufficiently high (assuming that the characteristics are combined such that a larger number is indicative of high confidence) to accept the base as being correct. It will be appreciated that the numerical value of this threshold will depend on many factors, including the units of the measurements used for the individual factors and the level of rigor which the individual user of the invention chooses to apply. Thus, it is not possible to give meaningful numerical examples of a threshold value. Preferably the threshold value should, however, be one which when applied in combination with the selected weights for the various factors to standard sequence (such as M13) produces error rates of less than 1/1,000 bases over the first 300 bases of the region sequenced.

It will be appreciated that the form of the confidence algorithm can be manipulated such that a "good" result will be either high or low. When the algorithm is such that a "good" result is large, then the numerical confidence value is "better" then the threshold if it exceeds the threshold. When the algorithm is such that a "good" result is small, then the numerical confidence value is better if it is less than the threshold. Similarly, in comparing the two numerical confidence values, the one that is "better" is one that is larger in the first circumstance and smaller in the second.

The application of the confidence values to the actual sequences is suitably performed in several successive steps. If the forward and reverse sequences do not confirm each other, then if a base exists (as opposed to a blank) in both the forward and reverse experimental sequences and the confidence measure of the better of the two is above the confidence threshold currently set, then that base with the higher confidence measure is assigned. If both bases are above the confidence threshold, an additional comparison to the reference sequence may be carried out, with the base which is the same as the reference being selected in this instance. Identity with the reference sequence is not a basis for selection as the correct base in an experimental sequence in the absence of a sufficient confidence value.

If only one of the experimental sequences has a base at the location of the deviation and there is a base (as opposed to a blank) in the reference sequence and the identified base in the experimental sequence is above the confidence threshold, then the base from the experimental sequence is used as the "correct" base (the base type in the reference sequence is ignored, only the spacing information is used). If there is a blank in the reference sequence and that is confirmed by either of the experimental sequences, then a blank should be put in the corrected sequence. If none of the above conditions apply, it is recommended to put an 'N' in the output sequence (standard letter denoting all bases are present) and mark the location as uncorrected.

The method of the invention is preferably carried out in an apparatus or system running appropriate computer code. The apparatus or system comprises at least a data processor operably programmed to perform the steps of identifying the sequence of bases within the forward and reverse data sets; comparing the sequence of bases within the forward and reverse data sets to identify any deviations from perfect complementarity in the sequences as determined for the two sets; and applying a confidence algorithm to each deviation to select the correct base from between the choices presented by the identified forward and reverse sequence. The apparatus or system further comprises means for obtaining forward and reverse data sets for the sample polynucleotide. In the case of an integrated system, this may be a direct data feed from an electrophoresis apparatus connected to the data processor. In a distributed system, the data sets can be obtained via a connection on a local area network (LAN), a wide area network (WAN), by modem or cable modem transmission or by insertion of a portable storage medium (diskette, tape etc.) into a drive capable of reading the portable storage medium. The apparatus or system further comprises means for providing useful output of the determined sequence. This may be as a video display or as a sequence listing stored on a storage medium such as a disk drive or read/write CD-ROM.

Figure 3:
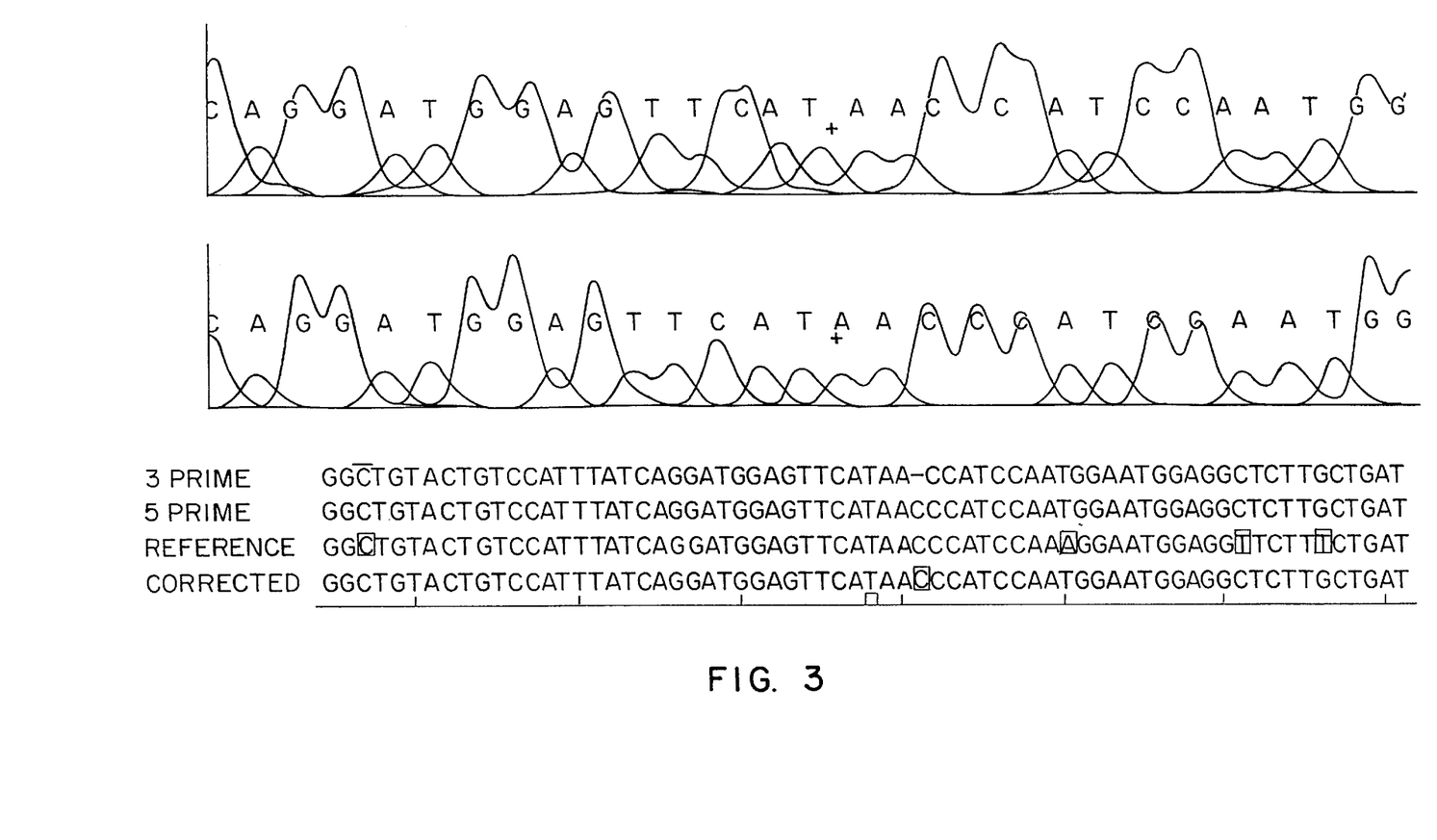
FIGS. 3 and 4 show a comparison of text files representing apparent base sequences (3 Prime sequence in FIG. 3=SEQ ID No. 1, 5 Prime sequence in FIG. 3=SEQ ID No. 2, Reference sequence in FIG. 3=SEQ ID No. 3,3 Prime sequence in FIG. 4=SEQ ID No. 4, 5 Prime sequence in FIG. 4=SEQ Id No. 5, Reference sequence in FIG.4=SEQ ID No. 6, and Corrected sequence in FIG.4=SEQ ID No. 7)
Figure 4:
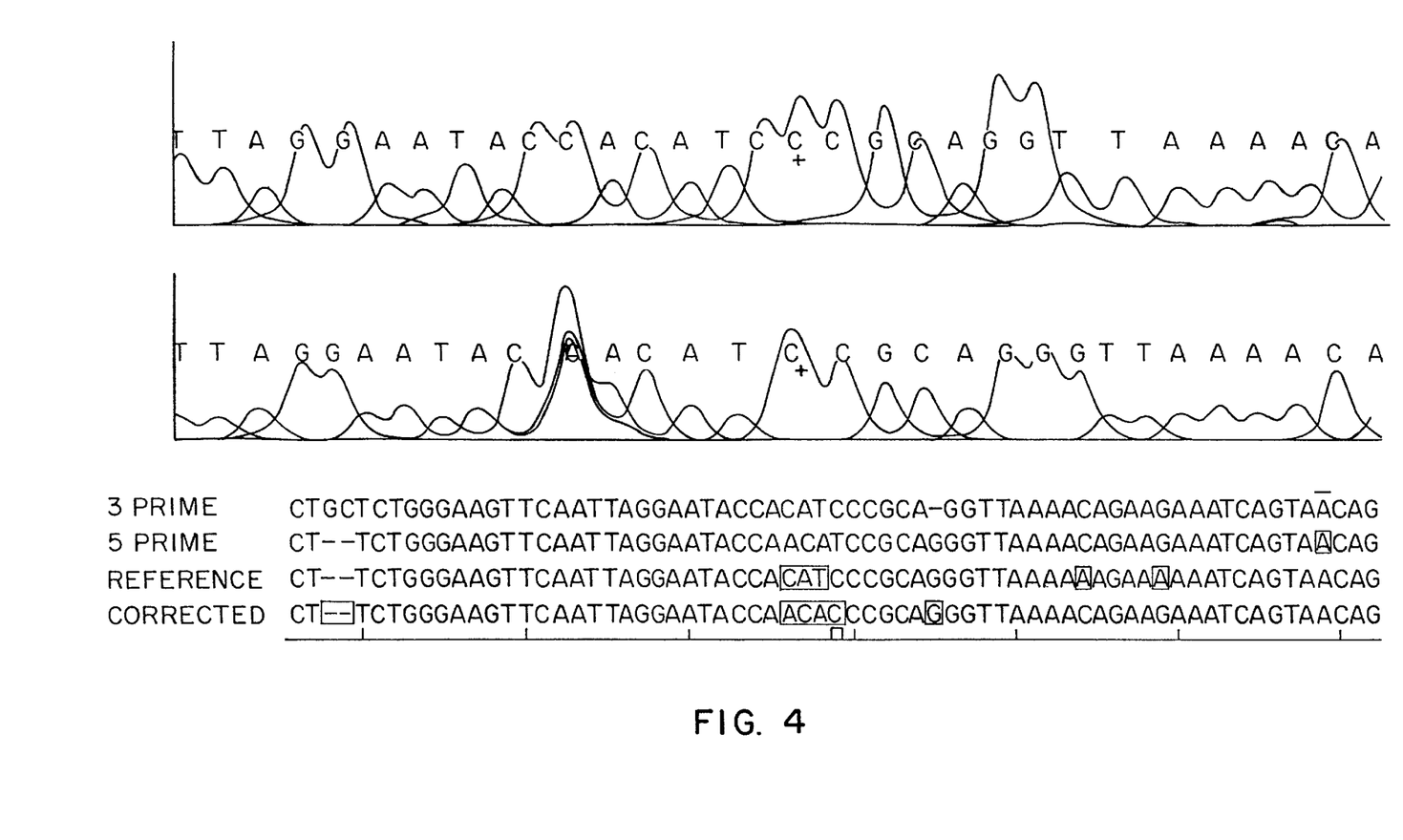

FIGS. 3 and 4 show screen output from an Intel® processor-based Hewlett-Packard Vectra VL computer (running an OpenStep Mach operating system) in which one amplicon of the RT region is being corrected for sequencing errors by analyzing both strands (shown as 3 prime (text 1) and 5 prime (text 2)). The highlighted bases on the reference show places of disagreement between the two strands (text 1 and text 2). The highlighted text in the Corrected area represent corrections according to the above embodiment of the present invention. In this case, the software allows adjustment of the confidence threshold, which as shown is set to 80%.

Figure 5:
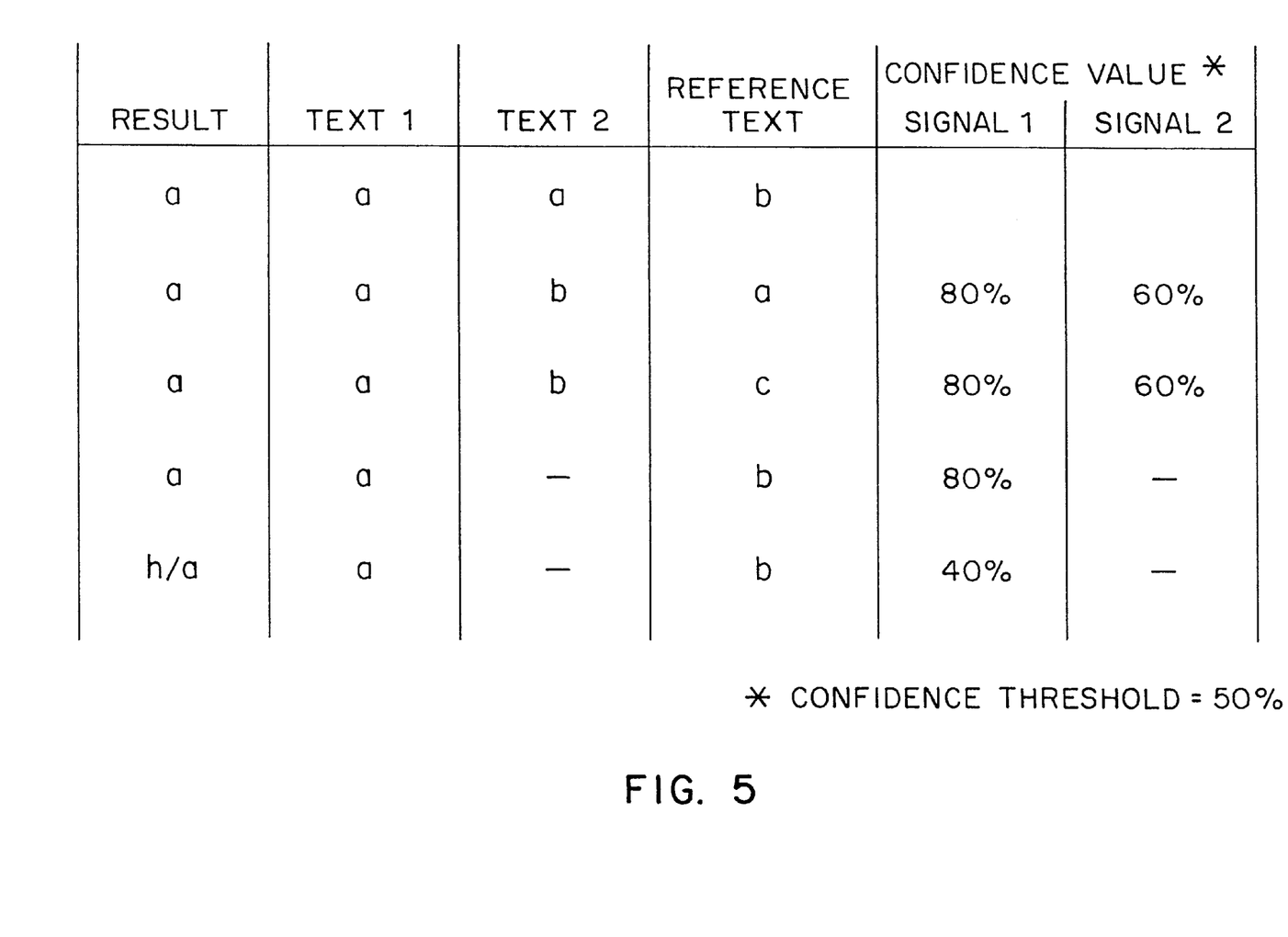
FIG. 5 shows a schematic representation of the deviation between forward (SEQ. ID No. 8) and reverse (SEQ. ID No. 9) sequences is observed.

FIG. 5 shows a chart indicating possible outcomes if basecall for a particular base is not confirmed by each strand. In this case, if the base in text 1 and text 2 are a, then they have confirming sequence (e.g. forward strand is A and reverse strand is T). N/A means that the confidence value for a particular base for either strand was below threshold (50% in this figure) and correction was not possible.

Figure 6:
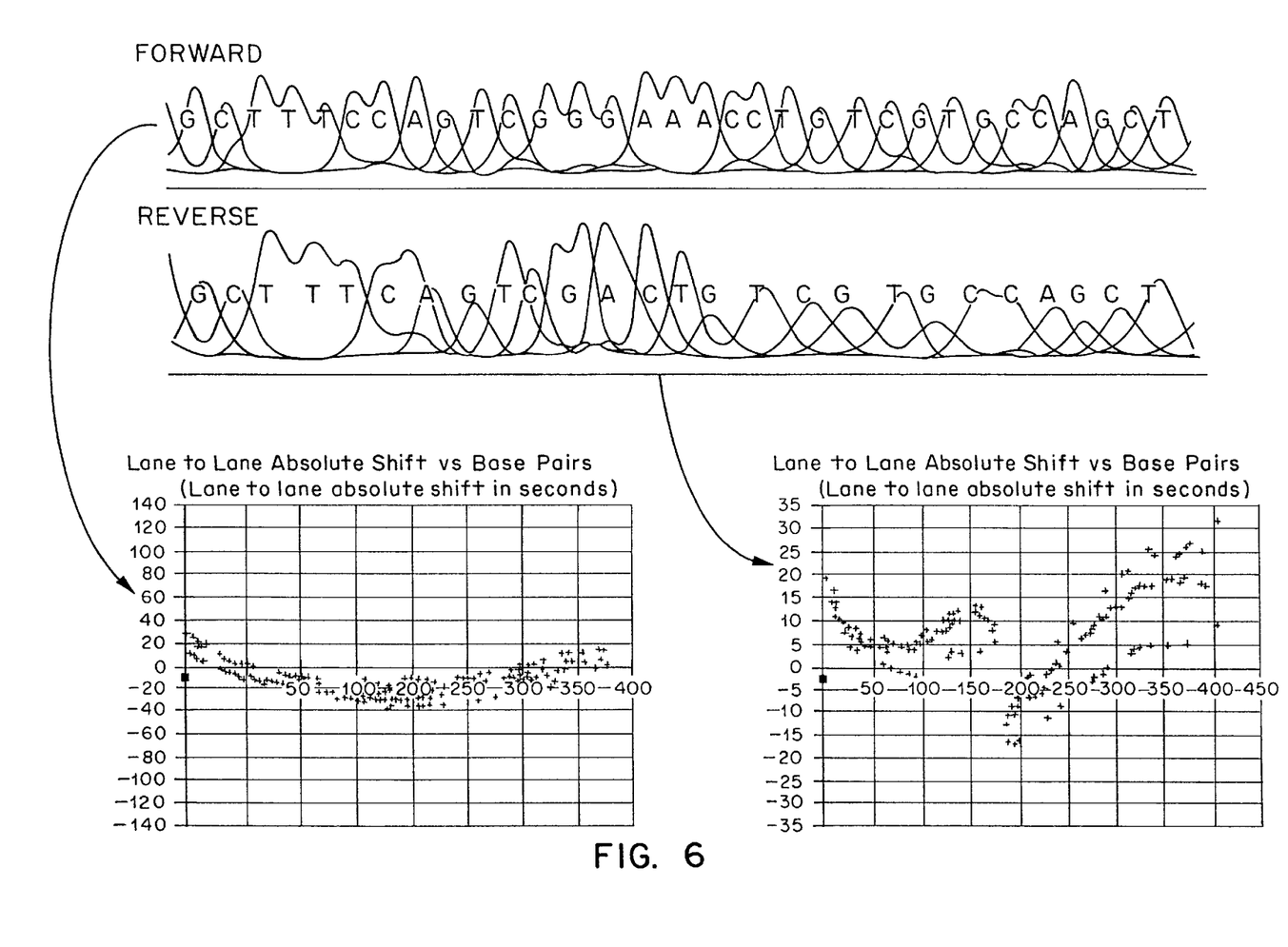
FIG. 6 shows sequence data for forward and reverse strands in which regularity/evenness of peak separation can be used as a key characteristic in determining a numerical confidence value.

FIG. 6 shows sequence data for the forward and reverse strand in which the parameter of "regularity/evenness of peak separation" has been measured as lane-to-lane shift in seconds (y-axis) with the base location on the x-axis. The reverse strand shows an erratic shift in lane timing and indicates a compression in signals which is unreliable. In contrast, this parameter shows more regular peak separation in the forward strand which may provide for an overall higher confidence value for bases on the forward strand.

In the course of evaluating the method and system of the invention with HIV sequence data, it has been observed that errors in the sequence data for one strand tend to be random with respect to errors in the sequence data of the opposite strand. As a result, it is less likely that an error will occur in the sequence data of both strands at the same base position. These errors can thereby be corrected should the reliability of one strand (confidence) be of a sufficient level. This observation highlights the utility of the present invention to create corrected sequence data in HIV genotyping, and it is believed that comparable benefits will be obtained for sequencing in general.

What is claimed is:

1. A method for determining the sequence of a sample nucleic acid polymer comprising the steps of:
   (a) obtaining forward and reverse data sets for forward and reverse strands of the sample nucleic acid, each data set containing a plurality of peaks reflecting the positions of A, C, G and T residues in the sample nucleic acid polymer, said data sets providing a migration time for each peak which migration time is related to the position of an A, C, G or T residue;
   (b) determining the apparent sequence of bases from the forward and reverse data sets;
   (c) comparing the apparent forward and reverse sequences of bases for perfect complementarity to identify any deviations from complementarity in the apparent sequences, any such deviation presenting a choice between two bases, only one of which is correct, and if a deviation is present identifying the peaks that are associated with the deviation;
   (d) applying a confidence algorithm to peaks associated with a deviation to arrive at a numerical confidence value for those peaks; and
   (e) comparing the numerical confidence values to each other and to a predetermined thresholds, and selecting as the correct base the base represented by the peak which has a better numerical confidence value, provided that the numerical confidence value is better than the threshold.

2. The method of claim 1, wherein the numerical confidence value results from a selected combination of two or more selected characteristics of each peak associated with a deviation.

3. The method of claim 2 wherein the characteristics are selected from among the following: separation between peaks; regularity/evenness of peak separation; peak height compared to neighbors, wherein a higher confidence is assigned if the peak heights are similar; peak area compared to neighbors, wherein a higher confidence is assigned if the peak areas are similar; distance to neighbors compared to the local average distance to neighbors; resolution of the peak, wherein a lower confidence is assigned for lower resolution; and signal to noise ratio in the region around the peak, wherein a lower confidence is assigned as the peak's size is more similar to the noise level.

4. The method of claim 2, wherein the numerical confidence value is a weighted combination of the selected characteristics.

5. The method of claim 4 wherein weights applied to each of the selected characteristics are initially determined for a combination of chemistry and instrumentation a plurality of calibration runs performed using the given combination of chemistry and instrumentation.

6. The method of claim 4, wherein weights applied to each of the selected characteristics are updated based upon accumulated data obtained when sequencing sample nucleic acid polymer.

7. The method of claim 1, wherein the numerical confidence results from a combination of at least the following characteristics of each peak associated with a deviation:
   separation distance between peaks;
   regularity/evenness of peak separation;
   peak height compared to neighbors;
   peak area compared to neighbors;
   distance to neighbors compared to the local average distance to neighbors;
   resolution of the peak; and
   signal-to-noise ratio in the region around the peak.

8. An apparatus for sequencing a sample nucleic acid polymer comprising:
   (a) a data processor;
   (b) means for obtaining forward and reverse data sets for the forward and reverse strands of the sample nucleic acid polymer for processing by the data processor, each data set containing a plurality of peaks reflecting the positions of A, C, G and T residues in the sample nucleic acid polymer, said data sets providing a migration time for each peak which migration time is related to the position of an A, C, G or T residue; and
   (c) means for providing output of sequencing information from the data processor;
   wherein the data processor is operatively programmed to process the forward and reverse data sets by a method including the steps of:
   determining the apparent sequence of bases from the forward and reverse data sets;
   comparing the apparent forward and reverse sequences of bases for perfect complementarity to identify any deviations from complementarity in the apparent sequences, any such deviation presenting a choice between two bases, only one of which is correct, and if a deviation is present identifying the peaks that are associated with the deviation;
   applying a confidence algorithm to the peaks associated with a deviation to arrive at a numerical confidence value for those peaks; and
   comparing the numerical confidence values to each other and to a predetermined threshold, and selecting as the correct base the base represented by the peak which has a better numerical confidence value, provided that the numerical confidence value is better than the threshold.

9. A method for determining the sequence of a sample nucleic acid polymer comprising the steps of:
   (a) obtaining forward and reverse data sets for forward and reverse strands of the sample nucleic acid by multiple cycles of a primer extension reaction in which two labeled primers are extended in the presence of chain terminating nucleotides in a single reaction mixture, each data set containing a plurality of peaks reflecting the positions of A, C, G and T residues in the sample nucleic acid, said data sets providing a migration time for each peak which migration time is related to the position of an A, C, G or T residue;

(b) determining the apparent sequence of bases from the forward and reverse data sets;

(c) comparing the apparent forward and reverse sequences of bases for perfect complementarity to identify any deviations from complementarity in the apparent sequences, any such deviation presenting a choice between two bases, only one of which is correct, and if a deviation is present identifying the peaks that are associated with the deviation;

(d) applying a confidence algorithm to the peaks associated with a deviation to arrive at a numerical confidence value for those peaks; and (e) comparing the numerical confidence values to each other and to a predetermined threshold, and selecting as the correct base the base represented by the peak which has a better numerical confidence value, provided that the numerical confidence value is better than the threshold.

* * * * *

SEQUENCE LISTING

<160> NUMBER OF SEQ ID NOS: 9

<210> SEQ ID NO 1
<211> LENGTH: 66
<212> TYPE: DNA
<213> ORGANISM: Human immunodeficiency virus
<220> FEATURE:
<223> OTHER INFORMATION: 3 Prime Reverse Transc riptase region

<400> SEQUENCE: 1
ggctgtactg tccatttatc aggatggagt tcataaccat ccaatggaat g gaggctctt      60 gctgat      66

<210> SEQ ID NO 2
<211> LENGTH: 67
<212> TYPE: DNA
<213> ORGANISM: Human immunodeficiency virus
<220> FEATURE:
<223> OTHER INFORMATION: 5 Prime Reverse Transc riptase region

<400> SEQUENCE: 2
ggctgtactg tccatttatc aggatggagt tcataaccca tccaatggaa t ggaggctct      60 tgctgat      67

<210> SEQ ID NO 3
<211> LENGTH: 67
<212> TYPE: DNA
<213> ORGANISM: Human immunodeficiency virus
<220> FEATURE:
<223> OTHER INFORMATION: Reverence Reverse Transcr iptase region

<400> SEQUENCE: 3
ggctgtactg tccatttatc aggatggagt tcataaccca tccaaaggaa t ggaggttct    60 ttctgat                                                              67

<210> SEQ ID NO 4
<211> LENGTH: 66
<212> TYPE: DNA
<213> ORGANISM: Human immunodeficiency virus
<220> FEATURE:
<223> OTHER INFORMATION: 3 Prime Reverse Transc riptase region

<400> SEQUENCE: 4
ctgctctggg aagttcaatt aggaatacca catcccgcag gttaaaacag a agaaatcag    60 taacag                                                               66

<210> SEQ ID NO 5
<211> LENGTH: 65
<212> TYPE: DNA
<213> ORGANISM: Human immunodeficiency virus
<220> FEATURE:
<223> OTHER INFORMATION: 5 Prime Reverse Transc riptase region

<400> SEQUENCE: 5
cttctgggaa gttcaattag gaataccaac atccgcaggg ttaaaacaga a gaaatcagt    60 aacag                                                                65

<210> SEQ ID NO 6
<211> LENGTH: 65
<212> TYPE: DNA
<213> ORGANISM: Human immunodeficiency virus
<220> FEATURE:
<223> OTHER INFORMATION: Reference Reverse Transcr iptase region

<400> SEQUENCE: 6
cttctgggaa gttcaattag gaataccaca tcccgcaggg ttaaaaaaga a aaatcagt     60 aacag                                                                65

<210> SEQ ID NO 7
<211> LENGTH: 65
<212> TYPE: DNA
<213> ORGANISM: Human immunodeficiency virus
<220> FEATURE:
<223> OTHER INFORMATION: Corrected Reverse Transcr iptase region

<400> SEQUENCE: 7
cttctgggaa gttcaattag gaataccaac acccgcaggg ttaaaacaga a gaaatcagt    60 aacag                                                                65

<210> SEQ ID NO 8
<211> LENGTH: 32
<212> TYPE: DNA
<213> ORGANISM: Human immunodeficiency virus
<220> FEATURE:
<223> OTHER INFORMATION: Forward strand

<400> SEQUENCE: 8
gctttccagt cgggaaacct gtcgtgccag ct                                  32

<210> SEQ ID NO 9
<211> LENGTH: 26

-continued

```
<212> TYPE: DNA
<213> ORGANISM: Human immunodeficiency virus
<220> FEATURE:
<223> OTHER INFORMATION: Reverse strand

<400> SEQUENCE: 9
gctttcagtc gactgtcgtg ccagct                                          26
```